United States Patent
Casano

(10) Patent No.: US 11,628,121 B2
(45) Date of Patent: Apr. 18, 2023

(54) COVER FOR CONCEALING MEDICAL EQUIPMENT FROM PATIENTS AND VISITORS

(71) Applicant: Ella Kathleen Casano, Fairfield, CT (US)

(72) Inventor: Ella Kathleen Casano, Fairfield, CT (US)

( * ) Notice: Subject to any disclaimer, the term of this patent is extended or adjusted under 35 U.S.C. 154(b) by 339 days.

(21) Appl. No.: 16/947,335

(22) Filed: Jul. 29, 2020

(65) Prior Publication Data

US 2020/0352824 A1 Nov. 12, 2020

Related U.S. Application Data

(63) Continuation of application No. 16/543,073, filed on Aug. 16, 2019, now Pat. No. 11,576,839.

(60) Provisional application No. 62/687,065, filed on Jun. 19, 2018.

(51) Int. Cl.
| | |
|---|---|
| *A61J 1/16* | (2023.01) |
| *A61J 1/14* | (2023.01) |
| *A61M 5/14* | (2006.01) |
| *A61J 1/10* | (2006.01) |
| *A63H 3/00* | (2006.01) |
| *A63H 3/02* | (2006.01) |

(52) U.S. Cl.
CPC ............... *A61J 1/16* (2013.01); *A61J 1/1462* (2013.01); *A63H 3/005* (2013.01); *A63H 3/02* (2013.01); *A61J 1/10* (2013.01); *A61M 5/1415* (2013.01); *A61M 5/1417* (2013.01)

(58) Field of Classification Search
CPC ............ A61M 2205/59; A61M 5/1415; A61M 5/1417; A61M 5/1414; A61M 5/14244; A61M 2005/1416; A61M 2025/028; A61M 2209/082; A61J 1/1462; A61J 1/16; A61J 9/0661; A61J 9/0692
See application file for complete search history.

(56) References Cited

U.S. PATENT DOCUMENTS

| | | | |
|---|---|---|---|
| 6,280,422 B1 * | 8/2001 | Sanchez-Browning | A61M 5/16877 215/11.4 |
| 6,520,466 B1 * | 2/2003 | Blanchard, III | G06F 1/1628 248/300 |
| 6,572,063 B1 * | 6/2003 | Gitelman | A61C 15/043 248/314 |
| 10,238,792 B1 * | 3/2019 | Macri | F16M 11/42 |
| 2001/0001188 A1 * | 5/2001 | Avner | A61B 3/12 181/126 |
| 2006/0011786 A1 * | 1/2006 | Finney | A63H 3/02 248/118 |
| 2006/0089077 A1 * | 4/2006 | Wittschen | A61J 7/0053 446/77 |
| 2008/0054132 A1 * | 3/2008 | Muncie | A61M 5/1415 248/176.1 |

(Continued)

*Primary Examiner* — Adam Marcetich
(74) *Attorney, Agent, or Firm* — Dunlap Bennett & Ludwig, PLLC

(57) ABSTRACT

A cover that conceals medical equipment with a backless configuration adapted to keep the medical equipment accessible to practitioners. The cover is further adapted to present a comforting front-facing component for the patient and/or visitors. The cover is made of medical grade plastic for preventing contamination and adverse reactions with the medical environment while facilitating sanitation of the cover.

7 Claims, 3 Drawing Sheets

(56) References Cited

U.S. PATENT DOCUMENTS

| | | | |
|---|---|---|---|
| 2008/0096459 A1* | 4/2008 | Mingle | A63H 3/005 |
| | | | 446/74 |
| 2008/0139076 A1* | 6/2008 | Frasier-Scott | A61M 5/14 |
| | | | 446/72 |
| 2011/0118666 A1* | 5/2011 | Sivilich | A61J 1/1462 |
| | | | 604/131 |
| 2014/0217138 A1* | 8/2014 | Kim | A61M 5/1417 |
| | | | 224/267 |
| 2014/0278156 A1* | 9/2014 | Thompson | A61M 5/1684 |
| | | | 235/375 |
| 2017/0030605 A1* | 2/2017 | Heller | F24F 11/58 |
| 2017/0296939 A1* | 10/2017 | Rivera | A61J 1/16 |
| 2018/0256449 A1* | 9/2018 | Moll | A61M 5/1415 |
| 2018/0353677 A1* | 12/2018 | Mager | A61M 5/1415 |

* cited by examiner

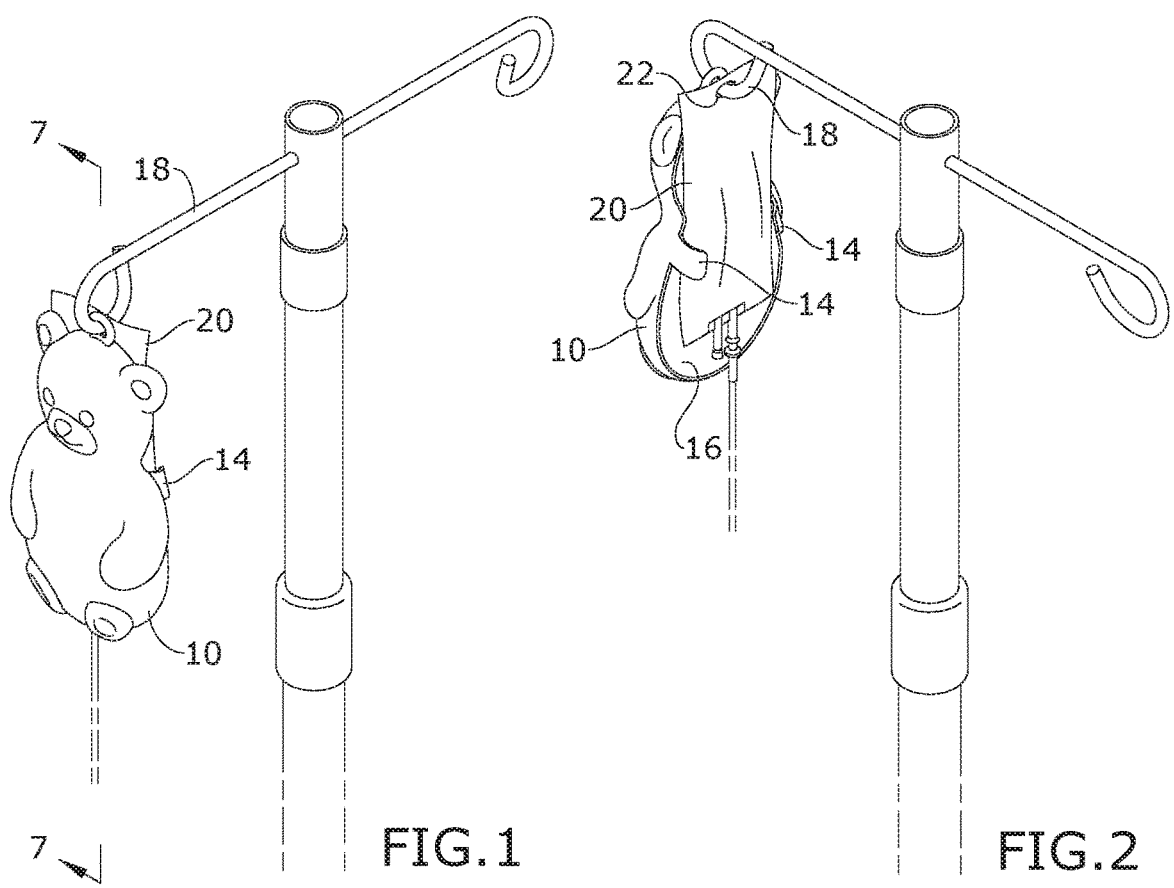
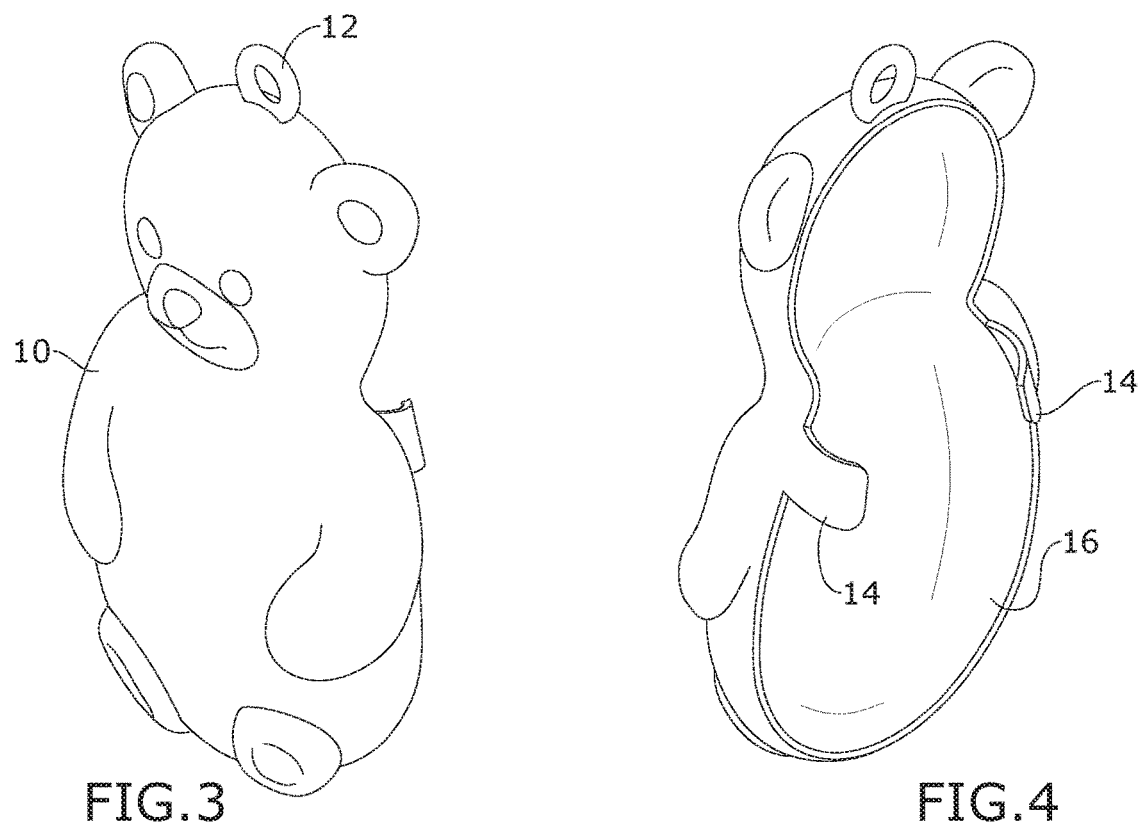

COVER FOR CONCEALING MEDICAL EQUIPMENT FROM PATIENTS AND VISITORS

CROSS-REFERENCE TO RELATED APPLICATION

This continuing application claims the benefit of priority of U.S. non-provisional application Ser. No. 16/543,073, filed 16 Aug. 2019, the contents of which are herein incorporated by reference.

BACKGROUND OF THE INVENTION

The present invention relates to medical devices and accessories and, more particularly, a cover adapted to both to conceal intravenous (IV) fluid bags or other medical equipment as well as to present to patients and/or their visitors a comforting and/or soothing appearance, while not promoting contamination and generally inert or non-reactive with the medical equipment and surrounding medical environment.

Millions of patients receive IV infusions and are afraid or overwhelmed at the sight of the medication and fluids bags dangling above them, like the sword of Damocles. Visitors or siblings may also be put off or even afraid to visit family members or other patients in the hospital due to unsightly medical equipment and fluids being delivered to the patient's veins by way of intravenous therapy.

With that said, one of the biggest concerns in hospitals is contamination of medical equipment that may spread to health-impaired patients. Another concern with medical equipment accessories is if they promote an adverse or caustic reaction with their surroundings. For instance, medical equipment covers that, say, provide a plush surface could raise infection control concerns and trigger precautions being taken regarding their (or their contaminants') reaction with medications. Also, a medical equipment cover that has a sleeve configuration would require the medical equipment/IV fluid bag to be fully inserted into the sleeve portion and could present an inconvenient nuisance for medical staff attempting to access the medical equipment/IV fluid bag.

As can be seen, there is a need for a medical equipment cover designed to conceal an IV fluid bag or other medical equipment through providing a "backless" configuration for not hindering access to the medical equipment by medical personnel. The medical equipment cover also provides a comfort-styled front presentation for patients and/or their visitors, yet the medical equipment cover does not promote contamination and is inert with the surrounding environment.

The medical equipment cover embodied by the present invention has small arms that cradle the medical equipment, such as the IV bag, facilitating access by caregivers. The medical equipment cover reduces the risk of contact with caustic medications, such as chemotherapy medicament that can leech onto other materials, through using medical grade plastic that can be wiped sterile with sanitation wipes and is inert with medical surroundings. The present invention can be sanitized between uses, and so is adapted to be reusable between patients, thereby keeping medical costs down.

The inventor's current US patent pending invention, the original stuffed-animal style IV cover ("Medi Teddy"™), is a stuffed animal sleeve that slips over a bag of medication of fluid. While well received and used widely, many hospitals will no longer allow this existing item out of an abundance of caution due to COVID-19 and infection control risks associated with plush stuffed animal material.

The present invention is made of medical grade plastic which can be cleansed with sanitation-wipes in the same way as IV pumps, tray tables, and toilet seats would be between patients. In other words, medical grade plastic can withstand harsh chemical cleaning with bleach or sani-wipes. The present invention also has a different attachment design from what currently exists in that the present invention is adapted to hang on structure associated with the medical equipment, as opposed to over the medical equipment, thereby the present invention does not affix directly to the medication by way of a pouch or sleeve; rather, the invention's "arms" gently cradle the medical equipment in place, thereby enabling access to a substantial portion of the medical equipment due to a rear access "backless": design.

The original, plush Medi Teddy is designed for patients who have repeat infusions over time. It is a partner in care and can be machine washed and brought to and from infusions. It is beneficial in that it belongs to the patient and bonding can occur over time. However, since it is not reusable, and not shared between patients, it precludes an entire class of short: term patients (those who need an IV once for only a few hours, a same-day surgery, or brief ambulance ride) from receiving one. The "new, plastic, reusable Medi Teddy" embodied in the present invention may be widely used in environments where patients do not need chronic infusions, but may still benefit from its use such as: emergency rooms, same day surgery centers, outpatient surgery units, and ambulances.

In short, the present invention provides a more pleasant, comforting, possibly familiar visual experience for patients and their visitors during a stressful time, while sterilely concealing the medical equipment (IV fluid bag) and medication being applied (infused).

SUMMARY OF THE INVENTION

In one aspect of the present invention, a backless cover for concealing medical equipment with a comfort object includes the following: a front surface having three-dimensional contours; a rear surface defining an equipment cavity for at least partially receiving medical equipment, the front and the rear surfaces facing opposing relative directions; a periphery interfacing the front and the rear surfaces; and a loop extending upwardly from an upper portion of the periphery, whereby a backless configuration of the backless cover facilitates access to the medical equipment.

In another aspect of the present invention, the backless cover for concealing an intravenous (IV) fluid bag with a comfort object includes the following: a front surface made of medical grade plastic having three-dimensional contours that define a comfort object; a rear surface made of medical grade plastic, the three-dimensional contours defining an equipment cavity along the rear surface, the equipment cavity dimensioned to partially receive the IV fluid bag, the front and the front surfaces facing opposing relative directions; a periphery interfacing the front and the rear surfaces; a loop extending upwardly from an upper portion of the periphery; and two gripping arms spaced apart along and extending from the periphery, whereby a backless configuration of the backless cover facilitates access to the IV fluid bag.

In yet another aspect of the present invention, a method of comforting an individual disturbed by an intravenous fluid bag, the method includes the following: providing the above-mentioned backless cover for concealing an intravenous (IV) fluid bag with a comfort object; engaging the loop with a pole associated with the IV fluid bag; receiving a portion of the IV fluid bag in the equipment cavity; and urging the two gripping arms to selectively engage the IV fluid bag so that the comfort object is at a desired elevation relative to the IV fluid bag.

These and other features, aspects and advantages of the present invention will become better understood with reference to the following drawings, description and claims.

BRIEF DESCRIPTION OF THE DRAWINGS

FIG. 1 is a front perspective view of an exemplary embodiment of the present invention, shown in use;

FIG. 2 is a rear perspective view of an exemplary embodiment of the present invention, shown in use;

FIG. 3 is a front perspective view of an exemplary embodiment of the present invention;

FIG. 4 is a rear perspective view of an exemplary embodiment of the present invention;

DETAILED DESCRIPTION OF THE INVENTION

Figure 5:
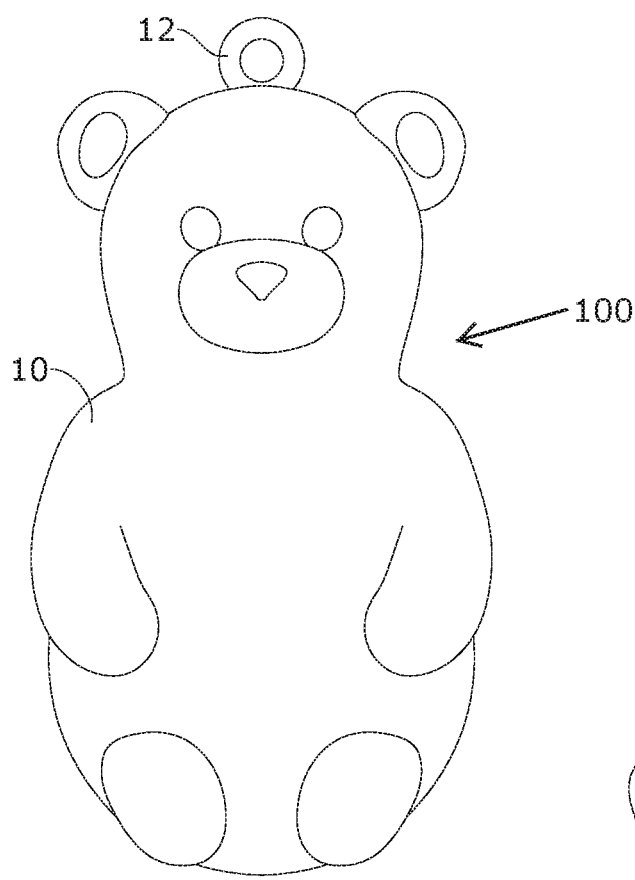
FIG. 5 is a front view of an exemplary embodiment of the present invention.
Figure 6:
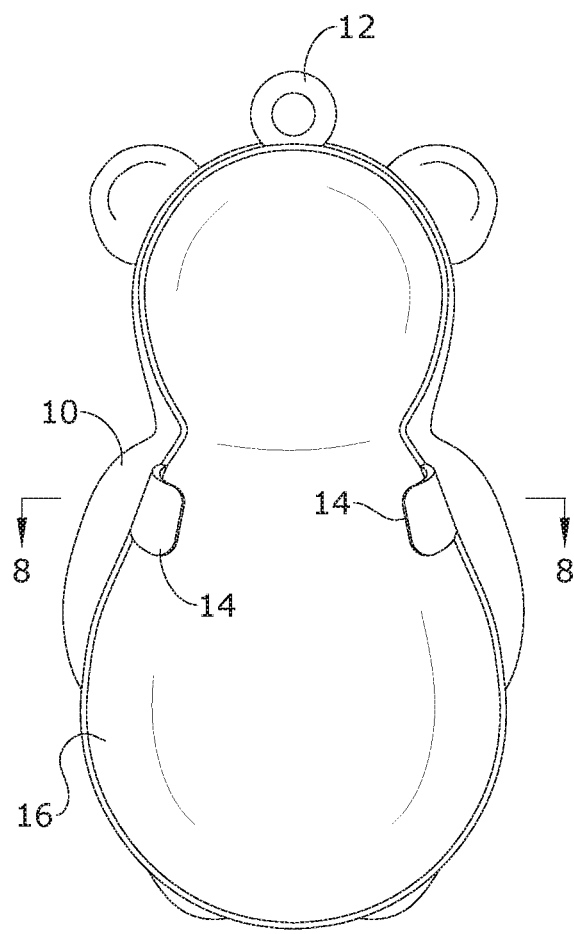
FIG. 6 is a rear view of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a cover that conceals medical equipment with a backless configuration adapted to keep the medical equipment accessible to practitioners, while presenting a comforting front-facing component for the patient and/or visitors. The cover is made of medical grade plastic for preventing contamination and adverse and adverse reactions with the medical environment while facilitating sanitation of the cover.

Referring now to FIGS. 1 through 8, the present invention may include a medical equipment cover 100 for providing comfort to patients using the medical equipment 20.

The medical equipment cover 100 may include a front surface 10 and a rear surface 16 that generally interface along a periphery 30. Thus, the periphery 30 may define an edge or interface between the front surface 10 and the rear surface 16. The front surface 10 may define a comfort object, which may include but is not limited to an animal-style shaped three-dimensional contours. It being understood that the comfort object may define or suggest an animal, like a teddy bear, or an animated character, plant, celestial object and the like.

The front surface 10 may be made of one or more of various medical grade plasticized materials that are receptive to sanitization, such as sanitation wipes. The selected medical grade plasticized material may be adaptive for injection molding, additive manufacturing or other forms of manufacturing.

The rear surface 16 may define an equipment cavity dimensioned and adapted to receive, at least in part, medical equipment 20. The medical equipment 20 may be, but is not limited to, an intravenous fluid bag in certain embodiments.

Figure 7:
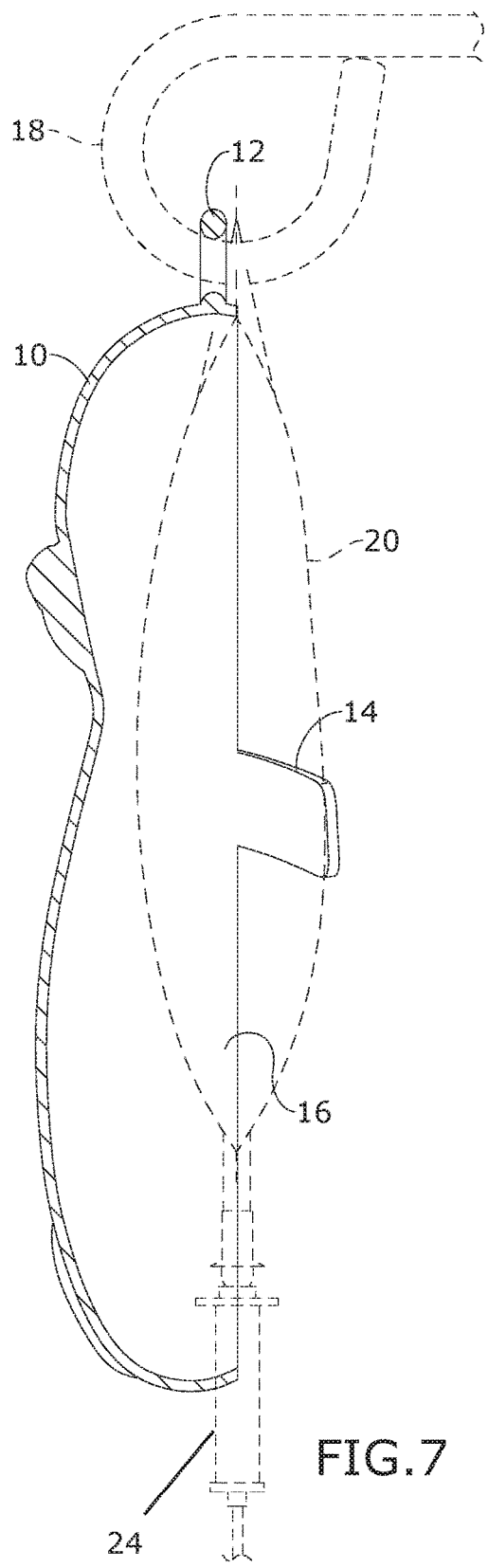
FIG. 7 is a section view of an exemplary embodiment of the present invention, taken along lines 7-7 in FIG. 1, with medical equipment shown in dashed lines for clarity.
Figure 8:
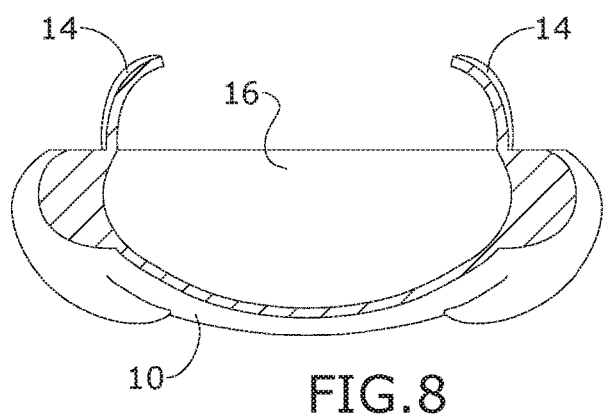
FIG. 8 is a section view of an exemplary embodiment of the present invention, taken along lines 8-8 in FIG. 6.

Along different lateral portions of the periphery 30, typically but not always along opposing lateral portions, gripping arms 14 may project therefrom. In certain embodiments, each gripping arm 14 may have a curvature that is directed both away from the front surface 10 and inward toward a longitudinal axis of the equipment cavity. Each arm 14 may be elasticized in such a way as to be movable by urging between various new positions and remain biased in each selected new position once said urging is removed; for instance, each gripping arm is movable between a first resting position (as illustrated in FIG. 8) and a second biased position outward of the periphery (as illustrated in FIG. 7). Thereby, each arm 14 may be moved out of the way so that the medical equipment 20 may be received in the equipment cavity, and then the arm 14 may be moved to engage a portion of the medical equipment 20.

Along an upper portion of the periphery 30 a loop 12 may be provided. The loop 12 may be endless or in certain embodiments may provide a gap for receiving structure of the medical equipment for the loop 12 to engage as illustrated in the Figures.

A method of using the present invention may include the following. The medical equipment cover 100 disclosed above may be provided in cases where a patient would feel better if a portion of medical equipment 20 where concealed and/or covered with a comfort object. For instance, if a young patient is hospitalized and needs intravenous (IV) therapy that delivers fluids directly into a vein, the fluid bag for said IV therapy could be the medical equipment 20. In this case, the fluid bag could be partially or completely received by the equipment cavity so that the front surface 10 faces the patient and/or visitors. Before or after receiving the fluid bag, the loop 12 may engage the IV pole 18. Typically, such IV poles 18 have hooks from which to hang the fluid bag, and so the loop 12 could hang from the same hook, as illustrated in FIGS. 1, 2, and 7. Then arms 14 could be urged to wrap around a portion of the fluid bag so as to secure thereto. The functionality of the arms 14 enables selective positioning of the front surface 10 (and associated comfort object) along the fluid bag, whereby the elevation of the front surface 10 relative to the fluid bag is not solely dependent on the loop 12/hook engagement.

When finally secured to the fluid bag, the coupled delivery equipment 24 is allowed to continue to the patient in an undisturbed and an easily accessible manner. The medical equipment cover 100 affords rear accessibly to the fluid bag/medical equipment 20 which is unconstructed and unconstrained by the "backless" configuration of medical equipment cover 100. The medical equipment cover 100 also obstructs the view of the medical equipment from the patient, and in fact replaces such a possibly disturbing view with a friendly appearance provided by the comfort object.

It should be understood, of course, that the foregoing relates to exemplary embodiments of the invention and that modifications may be made without departing from the spirit and scope of the invention as set forth in the following claims.

What is claimed is:

1. A comfort system for comforting a patient of intravenous (IV) therapy through an IV bag, the comfort system comprising:
   a rear-accessible cover having a front surface having three-dimensional contours that define a comfort object;
   a rear surface defining an equipment cavity dimensioned to completely receive the IV bag, the front and the rear surfaces facing opposing relative directions;
   a periphery interfacing the front and the rear surfaces;
   a loop extending upwardly from an upper portion of the periphery;
   two gripping arms spaced apart along and extending from lateral portions the periphery, wherein each gripping arm is elasticized to be movable between a first resting position and a second biased position outward of the periphery,
   whereby the IV bag accesses the equipment cavity laterally from the rear of the cover.

2. The comfort system of claim 1, wherein the front and the rear surfaces are made of medical grade plastic.

3. The comfort system of claim 1, wherein the two gripping arms are opposed to each other.

4. A method of comforting an individual disturbed by an intravenous fluid bag, the method comprising:
   providing the backless cover for concealing an intravenous (IV) fluid bag with a comfort object of claim 1;
   engaging the loop with a pole associated with the IV fluid bag;
   receiving a portion of the IV fluid bag in the equipment cavity; and
   urging the two gripping arms to selectively engage the IV fluid bag so that the comfort object is at a desired elevation relative to the IV fluid bag.

5. A backless cover for concealing an intravenous (IV) fluid bag with a comfort object, comprising:
   a front surface made of medical grade plastic having three-dimensional contours that incorporates the comfort object in the front surface by defining a neck portion interconnecting a head portion and a body portion and, wherein a maximum body width of the body portion is greater than a maximum head width;
   a rear surface wherein the three-dimensional contours define an equipment cavity dimensioned to receive the IV fluid bag;
   a periphery interfacing the front and the rear surfaces;
   a loop extending upwardly from an upper portion of the periphery; and
   two gripping arms spaced apart along and extending from the periphery, wherein the two gripping arms are disposed closer to the neck portion than the maximum body width,
   whereby a backless configuration of the backless cover facilitates access to the IV fluid bag, and whereby the maximum body width and the relative disposition of the two gripping arms facilitates a user handling a delivery equipment operatively associated with a bottom of the IV bag when the delivery equipment is circumscribed by the periphery.

6. The backless cover of claim 5, wherein the maximum head width is greater than a maximum neck width of the neck portion.

7. The backless cover of claim 5, wherein each gripping arm has a continuous curvature directed both away from the front surface and inward toward a longitudinal axis of the equipment cavity.

* * * * *